United States Patent [19]

Ikezaki et al.

[11] 3,952,021
[45] Apr. 20, 1976

[54] α-(3,4-DIMETHOXYPHENE-THYLAMINOMETHYL)-3,4 OR 3,5-DIHYDROXYBENZYLALCOHOLS AND SALTS THEREOF

[75] Inventors: Muneyoshi Ikezaki, Ageo; Yasushi Okazaki; Nobuo Ito, both of Tokyo; Taku Nagao, Ageo; Masao Hoshiyama, Tokyo; Hiromichi Nakajima, Yono, all of Japan

[73] Assignee: Tanabe Seiyaku Co., Ltd., Osaka, Japan

[22] Filed: Apr. 22, 1974

[21] Appl. No.: 462,594

[30] Foreign Application Priority Data

Apr. 28, 1973 Japan................................ 48-48744

[52] U.S. Cl......................... 260/343.7; 260/501.11; 260/501.18; 260/501.19; 260/511; 260/566 F; 260/570.5 C; 260/592; 260/570.8 R; 424/280; 424/316; 424/330
[51] Int. Cl.²................. C07C 91/16; C07D 307/62
[58] Field of Search.................. 260/501.18, 570.6, 260/570.5 C, 343.7, 501.19, 501.11

[56] References Cited
UNITED STATES PATENTS

| | | | |
|---|---|---|---|
| 2,900,415 | 8/1959 | Biel................................. | 260/570.6 |
| 3,804,899 | 4/1974 | Ebnother et al................ | 260/570.6 |
| 3,869,474 | 3/1975 | Miura et al..................... | 260/570.6 X |

*Primary Examiner*—Robert V. Hines
*Attorney, Agent, or Firm*—Jordan B. Bierman; Linda Bierman; Kenneth J. Stempler

[57] ABSTRACT

A compound of the formula:

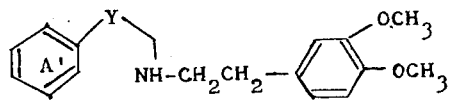

wherein Ring A' is dibenzyloxyphenyl and Y is carbonyl or hydroxymethylene, is subjected to catalytic hydrogenation. A compound of the formula:

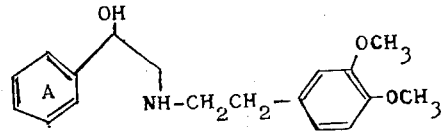

wherein Ring A is dihydroxyphenyl, is produced. The product is useful as a cardiotonic agent. It is also characterized by the high potency ratio of adrenergic $\beta_1$-receptor stimulating activity to adrenergic $\beta_2$-receptor stimulating activity.

5 Claims, No Drawings

α-(3,4-DIMETHOXYPHENETHYLAMINOMETHYL)-3,4 OR 3,5-DIHYDROXYBENZYLALCOHOLS AND SALTS THEREOF

This invention relates to a novel α-(3,4-dimethoxyphenethylaminomethyl)-dihydroxybenzylalcohol and a process for preparing same. More particularly, it relates to the compound of the formula:

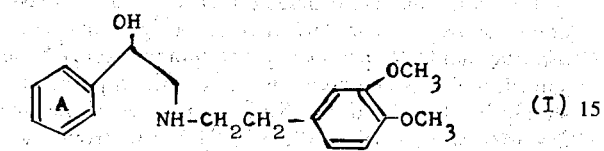

wherein Ring A is dihydroxyphenyl, or a pharmaceutically acceptable acid addition salt thereof.

It is known that adrenergic β-receptor stimulating action is devided into two groups; i.e., adrenergic $β_1$-receptor stimulating action [e.g., cardiac contractile activity (cardiac stimulation), positive chronotropic action(heart rate increase)], and adrenergic $β_2$-receptor stimulating action(e.g., bronchodilating, hypotensive, uterine smooth muscle-relaxing activities (c.f., "Nature" 214(1967), 597 – 598). For example, adrenergic $β_1$-receptor stimulants are useful as cardiotonics and adrenergic $β_2$-receptor stimulants are as bronchodilators or vasodilators. In this connection, John H. Biel et al discloses that α-(phenethylaminomethyl)-3,4-dihydroxybenzylalcohol, α-(α-methyl-phenethylaminomethyl)-3,4-dihydroxybenzylalcohol and α-(α-methyl-4-methoxyphenethylaminomethyl)-3,4-dihydroxybenzylalcohol are adrenergic β-receptor stimulants which are useful as bronchodilators and anti-spasmodics(U.S. Pat. Nos. 2,900,415 and 3,135,797). However, the clinical use of these compounds as cardiotonic agents is disadvantageous in that the cardiac contractile activity thereof is often accompanied and hampered by the unfavorable adrenergic $β_2$-receptor stimulating action(e.g., hypotension). As is clear from these facts, therefore, the development of cardiotonic agents having as few adrenergic $β_2$-receptor stimulating action as possible is considered to be of great importance.

We have now found that the α-(3,4-dimethoxyphenethylaminomethyl)-dihydroxybenzylalcohol (I) of the present invention is useful as a cardiotonic agent. That is, the compound (I) of the present invention has potent cardiac contractile activity and is especially characterized by the high potency ratio of adrenergic $β_1$-receptor stimulating activity to adrenergic $β_2$-receptor simulating activity. Further, the compound (I) of the present invention shows less positive chronotropic activity (i.e., less increase in heart rate) as compared with the cardiac contractile activity thereof. For example, when l-α-(3,4-dimethoxyphenethylaminomethyl)-3,4-dihydroxybenzylalcohol of the invention is injected into the femoral vein of male dogs at the dose of 0.1 μg/kg, said 3,4-dihydroxybenzylalcohol can increase the cardiac contractile force by 100 % without substantial influence upon the blood pressure. α-(3,4-Dimethoxyphenethylaminomethyl)-3,5-dihydroxybenzylalcohol of the invention, when examined under the same conditions as above, shows no substantial influence upon the blood pressure at the dose of 3 μg/kg which is necessary to 100 % increase of the cardiac contractile force. Concomitantly, as compared with α-(3,4,5-trimethoxyphenethylaminomethyl)-3,4-dihydroxybenzylalcohol disclosed in German Pat. application No. 2139516, the compound (I) of the present invention is more useful because of its higher potent cardiac contractile activity and/or less side effects.

According to the present invention, the α-(3,4-dimethoxyphenetylaminomethyl)-dihydroxybenzylalcohol (I) can be prepared by the steps of condensing a α-halo-dibenzyloxyacetophenone (II) with 3,4-dimethoxyphenethylamine (III) to give a α-(3,4-dimethoxyphenethylamino)-dibenzyloxyacetophenone (IV), optionally reducing the compound (IV) to give a α-(3,4-dimethoxyphenethylaminomethyl)dibenzyloxybenzylalcohol (V), and then subjecting the compound (IV) or (V) to catalytic hydrogenation. Alternatively, the α-(3,4-dimethoxyphenethylaminomethyl)-dihydroxybenzylalcohol (I) can be prepared by the steps of condensing a α,α-dihydroxy-dibenzyloxyacetophenone (VI-a) or sodium α-hydroxy-α-sulfo-dibenzyloxyacetophenone (VI-b) with 3,4-dimethoxyphenethylamine (III), reducing the resultant phenylalkylamine derivative (VII) to give a α-(3,4-dimethoxyphenethylaminomethyl)-dibenzyloxybenzylalcohol (V), and then subjecting the compound (V) to catalytic hydrogenation.

The above-mentioned reactions are shown by the following scheme:

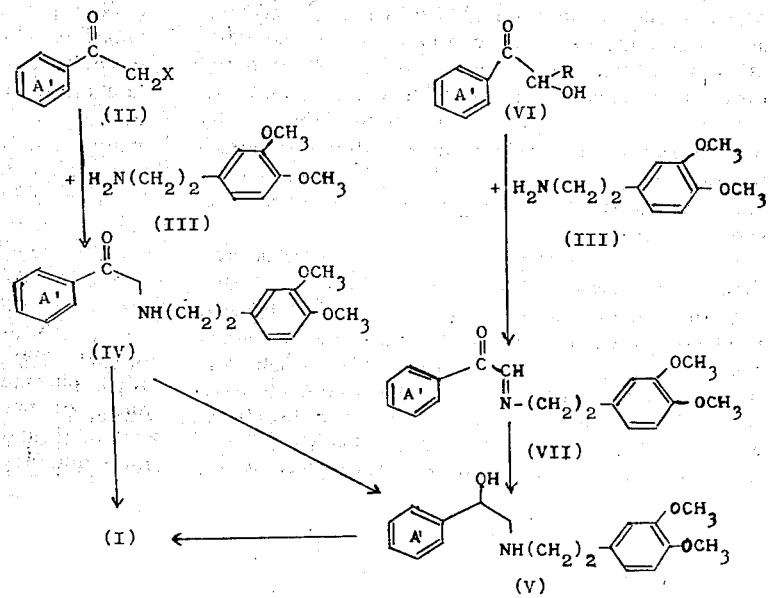

wherein Ring A' is dibenzyloxyphenyl, X is halogen atom and R is hydroxy or sodium sulfo($-SO_3Na$).

The starting compounds (II) and (VI) are readily obtainable. For example, the α-halo-dibenzyloxyacetophenone (II) is prepared by dropwise addition of sulfuryl chloride ($SO_2Cl_2$) to the methylene chloride solution of dibenzyloxyacetophenone at 0° to 30°C under stirring. The α,α-dihydroxydibenzyloxyacetophenone (VI-a) is prepared by refluxing for several hours a dioxane solution containing a dibenzyloxyacetophenone and selenium dioxide. The sodium α-hydroxy-α-sulfodibenzyloxyacetophenone (VI-b) is obtained as a crystalline precipitate by admixing the benzene solution of the compound (VI-a) with an aqueous sodium bisulfite ($NaHSO_3$) solution under vigorous agitation.

The condensation of the α-halo-dibenzyloxyacetophenone (II) with 3,4-dimethoxyphenethylamine (III) can be accomplished in a conventional manner. For example, the α-(3,4-dimethoxyphenethylamino)-dibenzyloxyacetophenone (IV) is prepared by admixing the compounds (II) and (III). The condensation reaction is conducted with or without a solvent. It is suitable to carry out the reaction at a temperature of 0° to 50°C, especially 20° to 30°C. Preferred examples of the reaction solvent include methylene chloride, chloroform, tetrahydrofuran and a lower alkanol(e.g., methanol, ethanol, propanol).

The condensation of the α,α-dihydroxy-dibenzyloxyacetophenone (VI-a) or sodium α-hydroxy-α-sulfodibenzyloxyacetophenone (VI-b) with 3,4-dimethoxyphenthylamine (III) is also accomplished in a conventional manner. For example, the phenylalkylamine derivative (VII) is preapred by admixing the compounds (VI-a or b) and (III) in a solvent. It is preferred to carry out the reaction at a temperature of 0° to 50°C, especially 30° to 40°C. Dioxane, tetrahydrofuran and a lower alkanol(e.g., methanol, ethanol, propanol) are suitable reaction solvents. If required, the condensation product (VII) thus obtained can be used for the subsequent reaction without isolating it from the reaction solution.

The α-(3,4-dimethoxyphenethylamino)-dibenzyloxybenzylalcohol (V) is prepared by reducing the resultant product (IV) or (VII) with an alkali metal borohydride or lithium aluminium hydride in a solvent. Lithium borohydride, potassium borohydride and sodium borohydride are employed as the alkali metal borohydride. When the alkali metal borohydride is employed as the reducing agent, a lower alkanol(e.g., methanol, ethanol, propanol, isopropanol) or a mixture of the lower alkanol and water is suitable as the reaction solvent. On the other hand, when lithium aluminium hydride is employed, tetrahydrofuran, ether and dioxane are suitable as the reaction solvent. It is preferred to carry out the reaction at a temperature of 0° to 50°C, especially 20° to 30°C.

The α-(3,4-dimethoxyphenethylaminomethyl)-dibenzyloxybenzylalcohol (V) is always obtained in the form of a racemic modification and may be, if required, resolved into each of its optically active enantiomers. The resolution of the compound (V) into each of its optically active enantiomers may be conducted by reacting the racemic modification of the compound (V) with a resolving agent in a solvent to form the diastereoisomeric salts thereof, and separating the diastereoisomers into each components thereof by selective crystallization. By said selective crystallization, the least soluble diastereoisomer is recovered as crystals from the reaction mixture and the more soluble one remains in the reaction mixture. It is preferred to carry out the selective crystallization at room temperature. Suitable examples of the resolving agents include d-tartaric acid or its derivatives(e.g., dibenzoyltartaric acid, monobenzoyltartaric acid, diacetyltartaric acid), d-camphorsulfonic acid, d-α-bromcamphorsulfonic acid, L-(−)-malic acid, l-mandelic acid, quinic acid, and dibasic amino acids or their derivatives (e.g., glutamic acid, aspartic acid, N-carbobenzyloxyglutamic acid). The solvent which is employed in the resolution procedure should be the one in which the solubilities of the two diastereoisomers are sufficiently different from each other. For this purpose, it is suitable to use water, a lower alkanol (e.g., methanol, ehtanol, n-propanol, isopropanol, n-butanol), ethyl acetate, acetic acid, dimethylformamide, or a mixture of water and either one of the lower alkanol, acetic acid or dimethylformamide.

The α-(3,4-dimethoxyphenethylamino)-dibenzyloxyacetophenone (IV) or α-(3,4-dimethoxyphenthylaminomethyl)-dibenzyloxybenzylalcohol (V), each of which is obtained in the above-mentioned procedures, is then subjected to catalytic hydrogenation to give the α-(3,4-dimethoxyphenethylaminomethyl)-dihydroxybenzylalcohol (I). Said hydrogenation is carried out in the presence of a catalyst in a hydrogen atmosphere. Preferred examples of the catalyst include platinum dioxide, platinum and palladium-carbon. A lower alkanol(e.g., methanol, ethanol, propanol, isopropanol) or a mixture of the lower alkanol and water is suitable as the reaction solvent. It is preferred to carry out the reaction at 10° to 30°C under atmospheric pressure.

The α-(3,4-dimethoxyphenethylaminomethyl)-dihydroxybenzylalcohol (I) can be used for pharmaceutical use either in the form of a racemic modification or in an optically active form. The α-(3,4-dimethoxyphenethylaminomethyl)-dihydroxybenzylalcohol (I) can also be used for pharmaceutical use either as the free base or a salt thereof. The base and salt thereof are readily convertible from one to the other by conventional manner. Pharmaceutically acceptable salts are, for example, hydrochloride, hydrobromide, perchloride, nitrate, sulfate, phosphate, formate, acetate, propionate, glycollate, lactate, pyruvate, oxalate, ascorbate, hydroxymaleate, phenylacetate, aminobenzoate, methanesulfonate, malonate, succinate, maleate, fumarate, malate, citrate, tartarate, ethanesulfonate, benzenesulfonate, p-toluenesulfonate, sulfanilate, aspartate or glutamate. The α-(3,4-dimethoxyphenethylaminomethyl)-dihydroxybenzylalcohol (I) may be used in the form of a pharmaceutical preparation for enteral or parenteral administration. The dose of the compound (I) suitable for pharmaceutical use may be 0.05 μg/kg to 1 mg/kg, especially 10 μg/kg to 1 mg/kg (for enteral administration) or 0.05 μg/kg to 30 μg/kg(for parenteral administration). Moreover, the compound (I) of the present invention may be used in conjunction or admixture with a pharmaceutical excipient that is suitable for enteral or parenteral administration. The excipient selected should be the one that does not react with the compound (I) of the present invention. Suitable excipients include, for example, gelatin, lactose, glucose, sodium chloride, starch, magnesium stearate, talcum, vegetable oil, benzyl alcohol and gums. Other known medicinal excipients may be employed. The pharmaceutical preparation may be a solid dosage form such as a tablet, a coated tablet, a pill or a capsule, or a liquid dosage form such as a solution, a suspension or an emulsion. The pharmaceutical preparation may be sterilized and/or may contain auxiliaries such as preserving, stabilizing, wetting or emulsifying agents.

Practical and presently-preferred embodiments of the present invention are illustratively shown in the following Examples.

EXAMPLE 1

1. A solution of 10 g of sulfuryl chloride in 15 ml of methylene chloride is added dropwise to 60 ml of a methylene chloride solution containing 19.9 g of 3,4-dibenzyloxyacetophenone. The addition is carried out at 0° to 10°C under stirring. After fifteen minutes, the mixture is neutralized with an aqueous sodium carbonate solution. The methylene chloride layer is collected, dried and then concentrated to dryness. The residue thus obtained is recrystallized from ethanol. 17.0 g of α-chloro-3,4-dibenzyloxyacetophenone are thereby obtained. Yield: 78 % M.p. 89°C Analysis calculated for $C_{22}H_{19}O_3Cl$ C, 72.03; H, 5.22; Cl, 9.67 Found C, 72.27; H, 5.14; Cl, 9.81

2. A solution of 3 g of α-chloro-3,4-dibenzyloxyacetophenone in 4 ml of methylene chloride is added to 4.5 g of 3,4-dimethoxyphenethylamine at room temperature under stirring. The mixture is stirred for 20 minutes. Then, the mixture is evaporated to remove methylene chloride. A mixture of 20 ml of 10 % hydrochloric acid and 10 ml of ethanol is added to the residue thus obtained, and the resultant crystalline precipitate is collected by filtration. The precipitate is washed with ethanol and ether, successively. Then, the precipitate is dried. 3.5 g of α-(3,4-dimethoxyphenethylamino)-3,4-dibenzyloxyacetophenone hydrochloride are obtained. Yield: 67 % M.p. 197° − 200°C(decomp.) (recrystallized from 10 % hydrochloric acid-ethanol).

Analysis calculated for $C_{32}H_{34}O_5NCl$
C, 70.01; H, 6.25; N, 2.56; Cl, 6.47 Found C, 69.87; H, 6.19; N, 2.85; Cl, 6.68

3. To 40 ml of a methanol solution containing 2.73 g of α-(3,4-dimethoxyphenethylamino)-3,4-dibenzyloxyacetophenone hydrochloride is added a mixture of 0.2 g of sodium hydroxide, 0.5 ml of water and 40 ml of methanol under stirring. 0.19 g of sodium borohydride is added to the mixture. Then, the mixture is stirred at room temperature for 15 minutes. The reaction mixture is concentrated to dryness under reduced pressure. Water is added to the residue, and the aqueous mixture is extracted with ethylacetate. The extract is washed with water, dried and then concentrated to dryness. The residue thus obtained is recrystallized from a mixture of ethylacetate and n-hexane. 2.11 g of α-(3,4-dimethoxyphenethylaminomethyl)-3,4-dibenzyloxybenzylalcohol are obtained as crystals. Yield: 82 % M.p. 79° − 81°C Analysis calculated for $C_{32}H_{35}O_5N$ C, 74.81; H, 6.87; N, 2.73 Found C, 75.02; H, 6.81; N, 2.69

Hydrochloride: M.p. 183°C (recrystallized from 95 % isopropanol).

4. 3 g of α-(3,4-dimethoxyphenethylaminomethyl)-3,4-dibenzyloxybenzylalcohol hydrochloride are suspended in a mixture of 80 ml of isopropanol and 20 ml of water. One g of 10 % palladium-carbon is added to the suspension. Then, the mixture is subjected to catalytic hydrogenation in a hydrogen atmosphere at room temperature for 1 hour under atmospheric pressure. After the reaction is completed, the mixture is filtered to remove the catalyst. The filtrate is concentrated under reduced pressure, and the residue thus obtained is recrystallized from isopropanol. 2.1 g of α-(3,4-dimethoxyphenethylaminomethyl)-3,4-dihydroxybenzylalcohol hydrochloride are obtained. Yield: 90 % M.p. 98° − 109°C(decomp.)

Analysis calculated for $C_{18}H_{23}O_5N.HCl.(CH_3)_2CHOH$ C, 58.64; H, 7.50; N, 3.26; Cl, 8.25 Found C, 58.53; H, 7.47; N, 3.21; Cl, 8.19

EXAMPLE 2

1. α-(3,4-dimethoxyphenethylaminomethyl)-3,4-dibenzyloxybenzylalcohol is prepared in the same manner as described in Example 1-(3). 22.8 g of α-(3,4-dimethoxyphenethylaminomethyl)-3,4-dibenzyloxybenzylalcohol and 11.1 g of d-10-camphorsulfonic acid are dissolved in 170 ml of methanol under heating. Then, the solution is allowed to stand at room temperature overnight. Crystalline precipitate is collected by filtration, and the precipitate is recrystallized twice from methanol. 14.1 g of l-α-(3,4-dimethoxyphenethylaminomethyl)-3,4-dibenzyloxybenzylalcohol d-10-camphorsulfonate are obtained. M.p. 151° − 153°C $[\alpha]_D^{20}$ +6.65°(C=1.11, methanol) Free base(recrystallized twice from ethylacetate): M.p. 104° − 105°C $[\alpha]_D^{20}$ −14.0°(C=0.93, chloroform)

Hydrochloride(recrystallized from methanol): M.p. 188° − 189°C $[\alpha]_D^{20}$ −19.0°(C=1.08, methanol)

The mother liquor which is obtained after separation of l-α-(3,4-dimethoxyphenethylaminomethyl)-3,4-dibenzyloxybenzylalcohol d-10-camphorsulfonate is concentrated to dryness, and the residue obtained is recrystallized three times from ethanol. 12.8 g of d-α-(3,4-dimethoxyphenethylaminomethyl)-3,4-dibenzyloxybenzylalcohol d-10-camphorsulfonate are thereby obtained. M.p. 139° − 140°C $[\alpha]_D^{20}$ +18.2°(C=1.1, methanol) Free base(recrystallized three times from ethylacetate): M.p. 104° − 105°C. $[\alpha]_D^{20}$ +14.5°(C=1.06, chloroform)

Hydrochloride(recrystallized from methanol): M.p. 188° − 189°C $[\alpha]_D^{20}$ +19.2°(C=1.01, methanol)

2. One g of d-α-(3,4-dimethoxyphenethylaminomethyl)-3,4-dibenzyloxybenzylalcohol hydrochloride is suspended in a mixture of 40 ml of isopropanol and 10 ml of water. 0.33 g of 10 % palladium-carbon is added to the suspension. Then, the mixture is subjected to catalytic hydrogenation in a hydrogen atmosphere at room temperature for 40 minutes under atmospheric pressure. After the reaction is completed, the mixture is filtered to remove the catalyst. The filtrate is concentrated under reduced pressure, and the residue thus obtained is recrystallized from isopropanol. 0.62 g of d-α-(3,4-dimethoxyphenethylaminomethyl)-3,4-dihydroxybenzylalcohol hydrochloride is obtained. M.p. 92° − 95°C $[\alpha]_D^{20}$ +18.2°(C=0.604, water)

Analysis calculated for $C_{18}H_{23}O_5N.HCl.(CH_3)_2$-CHOH C, 58.64; H, 7.50; N, 3.26; Cl, 8.25 Found C, 58.41; H, 7.32; N, 3.16; Cl, 8.21

One g of $l$-$\alpha$-(3,4-dimethoxyphenethylaminomethyl)-3,4-dibenzyloxybenzylalcohol hydrochloride is treated in the same manner as described above, whereby 0.67 g of $l$-$\alpha$-(3,4-dimethoxyphenethylaminomethyl)-3,4-dihydroxybenzylalcohol hydrochloride is obtained. M.p. 90° – 94°C $[\alpha]_D^{20}$ −18.6°(C=0.45, water)

Analysis calculated for $C_{18}H_{23}O_5N.HCl.(CH_3)_2$-CHOH C, 58.64; H, 7.50; N, 3.26; Cl, 8.25 Found C, 58.40; H, 7.41; N, 3.30; Cl, 8.25

EXAMPLE 3

$\alpha$-(3,4-dimethoxyphenethylamino)-3,4-dibenzyloxyacetophenone hydrochloride is prepared in the same manner as described in Example 1-(2). 0.3 g of $\alpha$-(3,4-dimethoxyphenethylamino)-3,4-dibenzyloxyacetophenone hydrochloride is suspended in a mixture of 24 ml of isopropanol and 6 ml of water. 0.05 g of platinum dioxide is added to the suspension. Then, the mixture is subjected to catalytic hydrogenation in a hydrogen atmosphere for 7 hours under atmospheric pressure. After the reaction is completed, the mixture is filtered to remove the catalyst. The filtrate is concentrated under reduced pressure, and the residue thus obtained is recrystallized from aqueous isopropanol. 0.14 g of $\alpha$-(3,4-dimethoxyphenethylaminomethyl)-3,4-dihydroxybenzylalcohol hydrochloride is obtained. Yield: 74 % M.p. 98 – 109°C(decomp.)

EXAMPLE 4

1. A mixture of 6.5 g of selenium dioxide, 2 ml of water and 40 ml of dioxane is added to 40 ml of a dioxane solution containing 20.0 g of 3,4-dibenzyloxyacetophenone. The mixture is refluxed for 6 hours. Then, the mixture is filtered to remove insoluble materials. The filtrate is concentrated to dryness. The residue is dissolved in benzene, and the benzene solution is passed through the column of silica gel. The effluent thus obtained is concentrated to dryness. 16.5 g of $\alpha,\alpha$-dihydroxy-3,4-dibenzyloxyacetophenone are thereby obtained. Yield: 80 % M.p. 97° – 105°C Analysis calculated for $C_{22}H_{20}O_5$ C, 72.51; H, 5.53 Found C, 72.38; H, 5.31

2. 3.4 g of $\alpha,\alpha$-dihydroxy-3,4-dibenzyloxyacetophenone and 1.8 g of 3,4-dimethoxyphenethylamine are dissolved in 20 ml of dioxane. The solution is heated and then evaporated to remove dioxane. The residue is dissolved in 20 ml of ethanol. 0.5 g of sodium borohydride is added to the ethanol solution. Then, the ethanol solution is refluxed for 2 hours. After the reaction is completed, the solution is evaporated to remove ethanol. Water is added to the residue thus obtained, and the aqueous mixture is extracted with ethylacetate. The extract is washed with water, dried and then evaporated to remove solvent. The crystalline residue thus obtained is recrystallized from a mixture of ethylacetate and n-hexane. 4.2 g of $\alpha$-(3,4-dimethoxyphenethylaminomethyl)-3,4-dibenzyloxybenzylalcohol are obtained. Yield: 87 % M.p. 79° – 81°C $\alpha$-(3,4-dimethoxyphenethylaminomethyl)-3,4-dibenzyloxybenzylalcohol is treated in the same manner as described in Example 1-(4), whereby $\alpha$-(3,4-dimethoxyphenethylaminomethyl)-3,4-dihydroxybenzylalcohol is obtained.

EXAMPLE 5

1. A solution of 31 g of sodium bisulfite in 60 ml of water is added to 100 ml of a benzene solution containing 20 g of $\alpha,\alpha$-dihydroxy-3,4-dibenzyloxyacetophenone. The mixture is shaken vigorously for 30 minutes. After allowing the mixture to stand at room temperature for 12 hours, the resultant crystalline precipitate is collected by filtration. The precipitate is washed with water and isopropylether, successively, and then dried. 27 g of sodium $\alpha$-hydroxy-$\alpha$-sulfo-3,4-dibenzyloxyacetophenone are obtained. Yield: 77 % M.p. >300°C Analysis calculated for $C_{22}H_{19}O_9Na$ C, 58.66; H, 4.25 Found C, 58.32; H, 4.13

2. 17.8 g of sodium $\alpha$-hydroxy-$\alpha$-sulfo-3,4-dibenzyloxyacetophenone are suspended in 170 ml of dioxane, and 7.2 g of 3,4-dimethoxyphenethylamine are added thereto. The suspension is stirred at room temperature for 3 hours. 170 ml of an ethanol solution containing 2.5 g of potassium hydroxide are added to the suspension for 1.5 hours under ice-cooling. One hour later, 2.72 g of sodium borohydride are added gradually to the suspension. Then, the suspension is heated at 78°C for one hour. After the reaction is completed, the suspension is concentrated to dryness under reduced pressure. Water is added to the residue, and the aqueous mixture is extracted with ethylacetate. The extract is washed with water, dried and then concentrated to dryness under reduced pressure. The residue thus obtained is allowed to stand at room temperature to give crystals(11.6 g) of $\alpha$-(3,4-dimethoxyphenethylaminomethyl)-3,4-dibenzyloxybenzylalcohol. Yield: 56 % M.p. 79° – 81°C 3. 3.0 g of $\alpha$-(3,4-dimethoxyphenethylaminomethyl)-3,4-dibenzyloxybenzylalcohol hydrochloride are suspended in a mixture of 80 ml of isopropanol and 20 ml of water. One g of 10 % palladium-carbon is added to the solution. Then, the mixture is subjected to catalytic hydrogenation in a hydrogen atmosphere at room temperature for 1 hour under atmospheric pressure. After the reaction is completed, the mixture is filtered to remove the catalyst. The filtrate is concentrated to dryness under reduced pressure, and the residue thus obtained is recrystallized from aqueous isopropanol. 2.1 g of $\alpha$-(3,4-dimethoxyphenethylaminomethyl)-3,4-dihydroxybenzylalcohol hydrochloride are obtained. Yield: 90 % M.p. 98° – 109°C (decomp.)

EXAMPLE 6

1. A mixture of 2.2 g of selenium dioxide and 1 ml of water is added to 30 ml of a dioxane solution containing 7 g of 3,5-dibenzyloxyacetophenone. The mixture is refluxed for 6 hours. Then, the mixture is filtered to remove insoluble materials. The filtrate is concentrated to dryness, and the residue is dissolved in benzene. After the benzene solution is treated with activated carbon, said solution is evaporated to remove solvent. The residue thus obtained is dissolved in ether. Then, the ethereal solution is shaken vigorously with 20 ml of an aqueous solution containing 11 g of sodium bisulfite. The resultant crystalline precipitate is collected by filtration. The precipitate is washed with water, ethanol and ether, successively, and then dried. 7.0 g of sodium $\alpha$-hydroxy-$\alpha$-sulfo-3,5-dibenzyloxyacetophenone are thereby obtained. Yield: 74 %

2. 7.83 g of sodium $\alpha$-hydroxy-$\alpha$-sulfo-3,5-dibenzyloxyacetophenone are suspended in a mixture of 40 ml of dioxane and 40 ml of ethanol, and 3.15 g of 3,4- dimethoxyphenethylamine are added thereto at room temperature. The suspension is stirred at the same temperature for 2 hours. Then, 20 ml of an ethanol solution containing 1.14 g of potassium hydroxide are added dropwise to the suspension under ice-cooling. After the suspension is stirred for 30 minutes, 1.32 g of sodium borohydride are added gradually to the suspension. The suspension is further stirred at room temperature for 3 hours. The suspension is concentrated to dryness, and the residue thus obtained is dissolved in methylene chloride. The methylene chloride solution is washed with water, dried and then evaporated to remove solvent, whereby a viscous syrup of reddish brown color is obtained. This crude product is chromatographed on the column of aluminium dioxide, and the column is eluted with ether-methanol (19 : 1). The eluate is concentrated to dryness. Then, 2.5 g of viscous syrup thus obtained is crystallized from ether and ethylacetate. 2 g of α-(3,4-dimethoxyphenethylaminomethyl)-3,5-dibenzyloxybenzylalcohol are thereby obtained. Yield: 22.5 % M.p. 85° – 86°C Analysis calculated for $C_{32}H_{35}O_5N$ C, 74.81; H, 6.87; N, 2.73 Found C, 75.27; H, 7.02; N, 2.88

3. 1.4 g of α-(3,4-dimethoxyphenethylaminomethyl)-3,5-dibenzyloxybenzylalcohol hydrochloride are suspended in a mixture of 32 ml of isopropanol and 8 ml of water. 0.42 g of 10 % palladium-carbon is added to the solution. Then, the mixture is subjected to catalytic hydrogenation in a hydrogen atmosphere at room temperature for 1 hour under atmospheric pressure. After the reaction is completed, the mixture is filtered to remove the catalyst. The filtrate is concentrated under reduced pressure, and the residue thus obtained is recrystallized from a mixture of methanol and ether. 0.6 g of α-(3,4-dimethoxyphenethylaminomethyl)-3,5-dihydroxybenzylalcohol hydrochloride is obtained. Yield: 63.5 % M.p. 193° – 194°C Analysis calculated for $C_{18}H_{23}O_5N.HCl$ C, 58.45; H, 6.54; N, 3.79 Found C, 58.16; H, 6.71; N, 4.08

EXAMPLE 7

1. A mixture of 2.2 g of selenium dioxide and one ml of water is added to 30 ml of a dioxane solution containing 7 g of 2,4-dibenzyloxyacetophenone. The mixture is refluxed for 6 hours. Then, the mixture is filtered to remove insoluble materials. The filtrate is concentrated to dryness, and the oily residue is dissolved in benzene. After the benzene solution is treated with activated carbon, said solution is evaporated to remove solvent. The residue thus obtained is dissolved in ether. Then, the ethereal solution is shaken vigorously with 20 ml of an aqueous solution containing 11 g of sodium bisulfite. The resultant crystalline precipitate is collected by filtration. The precipitate is washed with water, methanol and ether, successively, and then dried. 7.5 g of sodium α-hydroxy-α-sulfo-2,4-dibenzyloxyacetophenone are obtained. Yield: 79 %

2. 6 g of sodium α-hydroxy-α-sulfo-2,4-dibenzyloxyacetophenone are suspended in a mixture of 60 ml of dioxane and 60 ml of ethanol, and 2.4 g of 3,4-dimethoxyphenethylamine are added thereto at room temperature. The suspension is stirred at the same temperature for 2 hours. Then, a solution of 0.93 g of potassium hydroxide in 20 ml of ethanol is added dropwise to the suspension under ice-cooling. After the suspension is stirred for 30 minutes, 1 g of sodium borohydride is added gradually to the suspension. The suspension is further stirred at room temperature for 2 hours. Then, the suspension is evaporated to remove solvent. The residue is dissolved in methylene chloride. The methylene chloride solution is washed with water, dried and then evaporated to remove solvent, whereby a viscous syrup of reddish brown color is obtained. Ethylacetate is added to the viscous syrup, and the resultant crystalline precipitate is collected by filtration to give 3.28 g of crude crystals. The crystals are recrystallized from ethylacetate. 2.6 g of α-(3,4-dimethoxyphenethylaminomethyl)-2,4-dibenzyloxybenzylalcohol are obtained. Yield: 37.7 % M.p. 116° – 117°C Analysis calculated for $C_{32}H_{35}O_5N$ C, 74.81; H, 6.87; N, 2.73 Found C, 74.66; H, 6.78; N, 2.69

3. 0.6 g of α-(3,4-dimethoxyphenethylaminomethyl)-2,4-dibenzyloxybenzylalcohol oxalate is suspended in a mixture of 40 ml of isopropanol and 10 ml of water. 0.2 g of 10 % palladium-carbon are added to the suspension. Then, the mixture is subjected to catalytic hydrogenation in a hydrogen atmosphere at room temperature for 2 hours under atmospheric pressure. After the reaction is completed, the mixture is filtered to remove the catalyst. The filtrate is concentrated under reduced pressure, whereby 0.39 g of α-(3,4-dimethoxyphenethylaminomethyl)-2,4-dihydroxybenzylalcohol oxalate is obtained as amorphous powder. Yield: 93 %

NMR-spectrum:
DMSO-$D_6$ +$D_2O$(60MC): 6.4 – 3.2 (m, 6H, methylene), 6.23 (S, 3H, —$OCH_3$), 6.20 (S, 3H, —$OCH_3$), 4.85 (m, 1H, methin), 3.4 – 3.8 (m, 2H, arom), 2.6 – 3.3 (m, 4H, arom) (Internal standard, Tetramethylsilane)

EXAMPLE 8

1. 4.8 g of sulfuryl chloride are added dropwise to 50 ml of a methylene chloride solution containing 9.8 g of 2,5-dibenzyloxyacetophenone. The solution is stirred at room temperature for 2 hours. The reaction solution is washed with water, an aqueous sodium bicarbonate solution and water, successively. Then, the reaction solution is dried and evaporated to remove solvent. The residue thus obtained is recrystallized from ethanol. 8.75 g of α-chloro-2,5-dibenzyloxyacetophenone are thereby obtained. Yield: 81 % M.p. 113° – 114°C Analysis calculated for $C_{22}H_{19}O_3Cl$ C, 72.03; H, 5.22; Cl, 9.66 Found C, 72.12; H, 5.35; Cl, 9.59

2. A solution of 5 g of α-chloro-2,5-dibenzyloxyacetophenone in 16 ml of methylene chloride is added to 7.4 g of 3,4-dimethoxyphenethylamine. The mixture is refluxed for 1 hour. After cooling, 10 ml of 10 % hydrochloric acid are added to the mixture. The mixture is stirred. The resultant crystalline precipitate is collected by filtration, washed with methanol and then recrystallized from ethanol. 2.1 g of α-(3,4-dimethoxyphenethylamino)-2,5-dibenzyloxyacetophenone hydrochloride are obtained. Yield: 28.2 % M.p. 194° – 196°C Analysis calculated for $C_{32}H_{33}O_5N.HCl$ C, 70.01; H, 6.25; N, 2.56 Found C, 70.05; H, 6.37; N, 2.55

3. 2.1 g of α-(3,4-dimethoxyphenethylamino)-2,5-dibenzyloxyacetophenone hydrochloride are suspended in 40 ml of isopropanol, and 0.44 g of sodium borohydride are added to the suspension. The suspension is stirred at room temperature for 2 hours. Then, the suspension is evaporated to remove solvent. Water is added to the residue, and the aqueous mixture is extracted with methylene chloride. The extract is washed with water, dried and then evaporated to remove solvent. The residue thus obtained is recrystallized from ethylacetate. 1.65 g of α-(3,4-dimethoxyphenethylaminomethyl)-2,5-dibenzyloxybenzylalcohol are obtained. Yield: 84 % M.p. 147° – 148°C Hydrochloride M.p. 153° – 154°C (recrystallized from ethanol)

Analysis calculated for $C_{32}H_{35}O_5N·HCl$ C, 69.87; H, 6.59; N, 2.55 Found C, 70.22; H, 6.67; N, 2.62

4. 0.96 g of α-(3,4-dimethoxyphenethylaminomethyl)-2,5-dibenzyloxybenzylalcohol hydrochloride is suspended in a mixture of 40 ml of isopropanol and 10 ml of water. 0.32 g of 10 % palladium-carbon is added to the suspension. Then, the mixture is subjected to catalytic hydrogenation in a hydrogen atmosphere at room temperature for 2 hours under atmospheric pressure. After the reaction is completed, the mixture is filtered to remove the catalyst. The filtrate is concentrated under reduced pressure, whereby 0.59 g of α-(3,4-dimethoxyphenethylaminomethyl)-2,5-dihydroxybenzylalcohol hydrochloride are obtained as amorphous powder. Yield: 91.5 %

NMR-spectrum:
$D_2O$(60MC): 6.5 – 7.3 (m, 6H, methylene), 6.15 (s, 6H, —$OCH_3$), 4.80 (m, 1H, methine), 3.0 – 3.3 (m, 6H, arom) (Internal Standard, Sodium 2,2-dimethyl-2-silapentane-5-sulfonate)

What is claimed is:
1. A compound of the formula

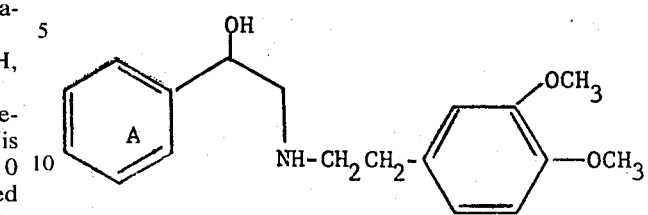

wherein Ring A is 3,4-dihydroxyphenyl, or 3,5-dihydroxyphenyl or a pharmaceutically acceptable acid addition salt thereof.

2. The compound of claim 1, wherein said compound is an optically active *l*-enantiomer.
3. The compound of claim 1, wherein Ring A is 3,4-dihydroxyphenyl.
4. The compound as claimed in claim 1, wherein Ring A is 3,5-dihydroxyphenyl.
5. *l*-α-(3,4-dimethoxypnenethylaminomethyl)-3,4-dihydroxybenzylalcohol or a pharmaceutically acceptable acid addition salt thereof.

* * * * *